United States Patent
Masui et al.

(10) Patent No.: US 6,320,026 B1
(45) Date of Patent: Nov. 20, 2001

(54) CELL GROWTH INHIBITOR FACTOR

(75) Inventors: Tohru Masui; Satoshi Yamaguchi, both of Tokyo (JP)

(73) Assignees: Japan as represented by Director General of National Institute of Health Sciences; Juridical Foundation, Japanese Foundation for Cancer Research, both of Tokyo (JP)

( * ) Notice: Subject to any disclaimer, the term of this patent is extended or adjusted under 35 U.S.C. 154(b) by 0 days.

(21) Appl. No.: 08/952,736

(22) PCT Filed: Mar. 28, 1997

(86) PCT No.: PCT/JP97/01087

§ 371 Date: Nov. 25, 1997

§ 102(e) Date: Nov. 25, 1997

(87) PCT Pub. No.: WO97/37019

PCT Pub. Date: Oct. 9, 1997

(30) Foreign Application Priority Data

Mar. 29, 1996 (WO) ..................................... PCT/JP96/00838

(51) Int. Cl.$^7$ .......................... C07K 14/00; C12N 15/00; A61K 38/00
(52) U.S. Cl. .......................... 530/350; 530/350; 530/399; 514/2; 514/12; 514/21; 514/44; 435/69.1
(58) Field of Search .................................. 424/94.1, 94.5; 435/69.1, 183, 320.1; 514/2; 536/23.1, 23.2; 935/22

(56) References Cited

U.S. PATENT DOCUMENTS 5,290,920 * 3/1994 Sindrey et al. ....................... 530/412
5,550,114 * 8/1996 Strayer .................................... 514/21
5,661,132 * 8/1997 Eriksson et al. ....................... 514/44

OTHER PUBLICATIONS

Rudinger (1976) Characteristics of the amino acids as components of a peptide hormone sequence. In: Peptide Hormones. Ed. J. A. Parsons. University Park Press, Baltimore, MD. pp. 1–7, Jun. 1976.*
Ngo et al. (1994) Computational complexity, protein structure prediction, and the ILevinthal paradox. In: The Protein Folding Problem and Tertiary Structure Prediction. Eds. Merz et al. Birkhauser et al. Boston, MA. pp. 491–495, Jan. 1994.*
Thornton et al. (1995) Protein Engineering: Editorial Overview. Current Opinion in Biotechnology 6(4): 367–369, Aug. 1995.*
Wallace (1993) Understanding cytochrome c function: engineering protein structure by semisynthesis. The FASEB Journal 7: 505–515, Apr. 1993.*
Proc. Natl. Acad. Sci. USA, vol. 82 (Jan. 1985) 119–123.
Nature, vol. 293 (Sep. 1981) 305–307.
In Vitro Cell. Div. Biol. Animal, vol. 31 (Jun. 1995) 440–446.
J. Stomatological Soc. of Japan, vol. 62 (1995) 78–93.
Genes & Development, vol. 9 (1995) 534–546.
Gene, vol. 145 (1994) 155–156.
EMBO Journal, vol. 10, No. 5 (1991) 1135–1147.
Mechanisms of Development, vol. 33 (1991) 27–38.

* cited by examiner

Primary Examiner—Karen Cochrane Carlson
Assistant Examiner—Patricia Robinson
(74) Attorney, Agent, or Firm—Fitzpatrick, Cella, Harper & Scinto

(57) ABSTRACT

The present invention relates to a polypeptide consisting of the amino acid sequence of SEQ ID NO: 1 or consisting of an amino acid sequence wherein one or more amino acids are deleted, replaced or added in the amino acid sequence of SEQ ID NO:1 and having cell growth inhibitory activity; DNA coding for the polypeptide; DNA hybridizing with DNA consisting of the nucleotide sequence of SEQ ID NO: 1 or 2 or with an oligonucleotide probe prepared based on the nucleotide sequence; a recombinant vector comprising the DNA; a transformant obtained by introducing the recombinant vector into host cells; a process for producing the polypeptide by culturing the transformant of the present invention in a medium; a pharmaceutical composition, preferably an anti-tumor agent, comprising the polypeptide as an active ingredient; a method of preventing or treating tumors comprising administering an effective amount of the polypeptide; and use of the polypeptide for producing a pharmaceutical composition useful for preventing or treating tumors.

12 Claims, No Drawings

```
                         SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
        (A) LENGTH: 927 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Homo sapiens
        (F) TISSUE TYPE: epithe cervix of the uteruselial tissues
             in the cervix of the uterus (ix) FEATURE:
        (A) NAME/KEY: CDS
        (B) LOCATION:1..927
        (C) IDENTIFICATION METHOD: E (ix) FEATURE:
        (A) NAME/KEY: cleavage-site
        (B) LOCATION:187..192, 335..340
        (C) IDENTIFICATION METHOD: S (xi) SEQUENCE DESCRIPTION: SEQ ID NO: 1:

ATG GAG CAA CTA CTA GGA ATA AAA CTT GGC TGC CTG TTT GCC CTG TTG       48
Met Glu Gln Leu Leu Gly Ile Lys Leu Gly Cys Leu Phe Ala Leu Leu
  1               5                  10                  15

GCT CTC ACT CTG GGC TGT GGC CTT ACT CCC ATC TGC TTC AAA TGG TTC       96
Ala Leu Thr Leu Gly Cys Gly Leu Thr Pro Ile Cys Phe Lys Trp Phe
             20                  25                  30

CAG ATT GAT GCA GCC AGA GGT CAT CAC CGG CGA GTC CTC AGA CTC CTG      144
Gln Ile Asp Ala Ala Arg Gly His His Arg Arg Val Leu Arg Leu Leu
         35                  40                  45

GGC TGT ATT TCT GCT GGT GTT TTC CTG GGA GCA GGG TTC ATG CAT ATG      192
Gly Cys Ile Ser Ala Gly Val Phe Leu Gly Ala Gly Phe Met His Met
     50                  55                  60

ACT GCT GAA GCC CTG GAG GAA ATT GAA TCA CAG ATT CAG AAG TTC ATG      240
Thr Ala Glu Ala Leu Glu Glu Ile Glu Ser Gln Ile Gln Lys Phe Met
```

```
                65                       70                      75                        80
          GTG CAG AAC AGA TCA GCA AGT GAG AGA AAT TCT TCT GGT GAT GCT GAT        288
          Val Gln Asn Arg Ser Ala Ser Glu Arg Asn Ser Ser Gly Asp Ala Asp
                          85                      90                       95

TCA GCT CAT ATG GAG TAT CCC TAT GGA GAG CTC ATC ATC TCC CTG GGC        336
          Ser Ala His Met Glu Tyr Pro Tyr Gly Glu Leu Ile Ile Ser Leu Gly
                          100                    105                     110

TTC TTT CTT GTC TTC TTT TTG GAG TCG CTG GCA TTG CAG TGC TGT CCT        384
          Phe Phe Leu Val Phe Phe Leu Glu Ser Leu Ala Leu Gln Cys Cys Pro
                      115                    120                     125

GGG GCT GCT GGA GGA TCG ACA GTG CAG GAC GAA GAA TGG GGT GGG GCT        432
          Gly Ala Ala Gly Gly Ser Thr Val Gln Asp Glu Glu Trp Gly Gly Ala
                  130                    135                     140

CAT ATC TTC GAA CTC CAC AGC CAT GGA CAT TTA CCC TCA CCC TCA AAG        480
          His Ile Phe Glu Leu His Ser His Gly His Leu Pro Ser Pro Ser Lys
          145                    150                     155                    160

GGT CCC CTC CGA GCC CTT GTC CTC TTG CTG TCA CTC TCC TTT CAC TCA        528
          Gly Pro Leu Arg Ala Leu Val Leu Leu Leu Ser Leu Ser Phe His Ser
                          165                     170                    175

GTG TTT GAA GGG CTA GCT GTG GGG CTG CAG CCG ACA GTA GCA GCT ACC        576
          Val Phe Glu Gly Leu Ala Val Gly Leu Gln Pro Thr Val Ala Ala Thr
                      180                     185                    190

GTG CAG CTC TGC CTT GCT GTC CTG GCT CAT AAG GGG CTT GTG GTG TTT        624
          Val Gln Leu Cys Leu Ala Val Leu Ala His Lys Gly Leu Val Val Phe
                      195                     200                    205

GGT GTA GGA ATG CGG CTA GTG CAT TTA GGT ACC AGC TCA CGA TGG GCA        672
          Gly Val Gly Met Arg Leu Val His Leu Gly Thr Ser Ser Arg Trp Ala
                  210                     215                    220

GTG TTC TCC ATA CTA TTA TTA GCT CTC ATG TCC CCC CTG GGC CTA GCC        720
          Val Phe Ser Ile Leu Leu Leu Ala Leu Met Ser Pro Leu Gly Leu Ala
          225                     230                    235                    240

GTA GGG CTG GCT GTG ACT GGA GGG GAC TCT GAA GGA GGG CGG GGC TTA        768
          Val Gly Leu Ala Val Thr Gly Gly Asp Ser Glu Gly Gly Arg Gly Leu
                          245                    250                     255

GCC CAG GCT GTG TTA GAG GGT GTG GCA GCT GGT ACC TTC CTG TAT GTC        816
          Ala Gln Ala Val Leu Glu Gly Val Ala Ala Gly Thr Phe Leu Tyr Val
                      260                     265                    270

ACC TTC CTA GAA ATT CTT CCA CGG GAG CTA GCT AGT CCT GAG GCC CCT        864
          Thr Phe Leu Glu Ile Leu Pro Arg Glu Leu Ala Ser Pro Glu Ala Pro
                      275                     280                    285

CTA GCT AAG TGG AGC TGT GTA GCC GCT GGT TTT GCC TTC ATG GCC TTT        912
          Leu Ala Lys Trp Ser Cys Val Ala Ala Gly Phe Ala Phe Met Ala Phe
                  290                     295                    300

ATT GCC TTG TGG GCC                                                    927
          Ile Ala Leu Trp Ala
          305
```

(2) INFORMATION FOR SEQ ID NO: 2:

(i) SEQUENCE CHARACTERISTICS:
        (A) LENGTH: 1356 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Homo sapiens
        (F) TISSUE TYPE: epithe cervix of the uteruselial tissues
            in the cervix of ts (ix) FEATURE:

-continued

```
    (A) NAME/KEY: CDS
    (B) LOCATION:131..1057
    (C) IDENTIFICATION METHOD: E (ix) FEATURE:
    (A) NAME/KEY: cleavage-site
    (B) LOCATION:317..322, 425..430
    (C) IDENTIFICATION METHOD: S (xi) SEQUENCE DESCRIPTION: SEQ ID NO: 2:
```

| | | |
|---|---|---|
| CTCGTCGAAC AGCCTCCTGA AACTCACGAG AGTGGACACT CCAGTGTTGA CCACCTAAGA | 60 | |
| TACCACTCCT GCTCCAAAGA TTACAGCTCC CTTGTCATTC TGACTCCTGG GCTTACCCTA | 120 | |

```
CACCCCAGAG ATG GAG CAA CTA CTA GGA ATA AAA CTT GGC TGC CTG TTT        169
           Met Glu Gln Leu Leu Gly Ile Lys Leu Gly Cys Leu Phe
            1               5                   10

GCC CTG TTG GCT CTC ACT CTG GGC TGT GGC CTT ACT CCC ATC TGC TTC        217
Ala Leu Leu Ala Leu Thr Leu Gly Cys Gly Leu Thr Pro Ile Cys Phe
        15                  20                  25

AAA TGG TTC CAG ATT GAT GCA GCC AGA GGT CAT CAC CGG CGA GTC CTC        265
Lys Trp Phe Gln Ile Asp Ala Ala Arg Gly His His Arg Arg Val Leu
 30                  35                  40                  45

AGA CTC CTG GGC TGT ATT TCT GCT GGT GTT TTC CTG GGA GCA GGG TTC        313
Arg Leu Leu Gly Cys Ile Ser Ala Gly Val Phe Leu Gly Ala Gly Phe
                 50                  55                  60

ATG CAT ATG ACT GCT GAA GCC CTG GAG GAA ATT GAA TCA CAG ATT CAG        361
Met His Met Thr Ala Glu Ala Leu Glu Glu Ile Glu Ser Gln Ile Gln
             65                  70                  75

AAG TTC ATG GTG CAG AAC AGA TCA GCA AGT GAG AGA AAT TCT TCT GGT        409
Lys Phe Met Val Gln Asn Arg Ser Ala Ser Glu Arg Asn Ser Ser Gly
         80                  85                  90

GAT GCT GAT TCA GCT CAT ATG GAG TAT CCC TAT GGA GAG CTC ATC ATC        457
Asp Ala Asp Ser Ala His Met Glu Tyr Pro Tyr Gly Glu Leu Ile Ile
     95                 100                 105

TCC CTG GGC TTC TTT CTT GTC TTC TTT TTG GAG TCG CTG GCA TTG CAG        505
Ser Leu Gly Phe Phe Leu Val Phe Phe Leu Glu Ser Leu Ala Leu Gln
110                 115                 120                 125

TGC TGT CCT GGG GCT GCT GGA GGA TCG ACA GTG CAG GAC GAA GAA TGG        553
Cys Cys Pro Gly Ala Ala Gly Gly Ser Thr Val Gln Asp Glu Glu Trp
                130                 135                 140

GGT GGG GCT CAT ATC TTC GAA CTC CAC AGC CAT GGA CAT TTA CCC TCA        601
Gly Gly Ala His Ile Phe Glu Leu His Ser His Gly His Leu Pro Ser
            145                 150                 155

CCC TCA AAG GGT CCC CTC CGA GCC CTT GTC CTC TTG CTG TCA CTC TCC        649
Pro Ser Lys Gly Pro Leu Arg Ala Leu Val Leu Leu Leu Ser Leu Ser
        160                 165                 170

TTT CAC TCA GTG TTT GAA GGG CTA GCT GTG GGG CTG CAG CCG ACA GTA        697
Phe His Ser Val Phe Glu Gly Leu Ala Val Gly Leu Gln Pro Thr Val
    175                 180                 185

GCA GCT ACC GTG CAG CTC TGC CTT GCT GTC CTG GCT CAT AAG GGG CTT        745
Ala Ala Thr Val Gln Leu Cys Leu Ala Val Leu Ala His Lys Gly Leu
190                 195                 200                 205

GTG GTG TTT GGT GTA GGA ATG CGG CTA GTG CAT TTA GGT ACC AGC TCA        793
Val Val Phe Gly Val Gly Met Arg Leu Val His Leu Gly Thr Ser Ser
                210                 215                 220

CGA TGG GCA GTG TTC TCC ATA CTA TTA TTA GCT CTC ATG TCC CCC CTG        841
Arg Trp Ala Val Phe Ser Ile Leu Leu Leu Ala Leu Met Ser Pro Leu
            225                 230                 235

GGC CTA GCC GTA GGG CTG GCT GTG ACT GGA GGG GAC TCT GAA GGA GGG        889
Gly Leu Ala Val Gly Leu Ala Val Thr Gly Gly Asp Ser Glu Gly Gly
        240                 245                 250
```

```
CGG GGC TTA GCC CAG GCT GTG TTA GAG GGT GTG GCA GCT GGT ACC TTC      937
Arg Gly Leu Ala Gln Ala Val Leu Glu Gly Val Ala Ala Gly Thr Phe
    255                 260                 265

CTG TAT GTC ACC TTC CTA GAA ATT CTT CCA CGG GAG CTA GCT AGT CCT      985
Leu Tyr Val Thr Phe Leu Glu Ile Leu Pro Arg Glu Leu Ala Ser Pro
270                 275                 280                 285

GAG GCC CCT CTA GCT AAG TGG AGC TGT GTA GCC GCT GGT TTT GCC TTC     1033
Glu Ala Pro Leu Ala Lys Trp Ser Cys Val Ala Ala Gly Phe Ala Phe
                290                 295                 300

ATG GCC TTT ATT GCC TTG TGG GCC TGAGAGATTC CTGGCTTTTC TGATGGACCT    1087
Met Ala Phe Ile Ala Leu Trp Ala
                305

ATTTAGGACA ACCTCTCTAT CCCCAGGGAG ACCTCCCAAA TGGCTTTGAC CCTCAGACAT   1147

TTCTTTACTC AGACTAAATA GCATTCAGTA GGACTGGACT GGACCCCAGG TTTCCTTTAC   1207

ATGAGATCCC ATTTCTCACC CTGGACTAAG ACAAAGATAT TTAGGTTGAG CAGCTATTAA   1267

TTGGAGAATT GGTACAGAGA CGCTCCAGAT TTTATTCTTA TCCCATTTAT GCTACTGTGT   1327

GTAATAAAAT GCCCATTTTA CCCTCCTTC                                    1356

(2) INFORMATION FOR SEQ ID NO: 3:

(i) SEQUENCE CHARACTERISTICS:
        (A) LENGTH: 255 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Homo sapiens
        (F) TISSUE TYPE: epithe cervix of the uteruselial tissues
            in the cervix of ts (ix) FEATURE:
        (A) NAME/KEY: CDS
        (B) LOCATION:1..255
        (C) IDENTIFICATION METHOD: E (xi) SEQUENCE DESCRIPTION: SEQ ID NO: 3:

ATG GAG CAA CTA CTA GGA ATA AAA CTT GGC TGC CTG TTT GCC CTG TTG       48
Met Glu Gln Leu Leu Gly Ile Lys Leu Gly Cys Leu Phe Ala Leu Leu
1               5                   10                  15

GCT CTC ACT CTG GGC TGT GGC CTT ACT CCC ATC TGC TTC AAA TGG TTC       96
Ala Leu Thr Leu Gly Cys Gly Leu Thr Pro Ile Cys Phe Lys Trp Phe
                20                  25                  30

CAG ATT GAT GCA GCC AGA GGT CAT CAC CGG CGA GTC CTC AGA CTC CTG      144
Gln Ile Asp Ala Ala Arg Gly His His Arg Arg Val Leu Arg Leu Leu
            35                  40                  45

GGC TGT ATT TCT GCT GGT GTT TTC CTG GGA GCA GGG TTC ATG CAT ATG      192
Gly Cys Ile Ser Ala Gly Val Phe Leu Gly Ala Gly Phe Met His Met
    50                  55                  60

ACT GCT GAA GCC CTG GAG GAA ATT GAA TCA CAG ATT CAG AAG TTC ATG      240
Thr Ala Glu Ala Leu Glu Glu Ile Glu Ser Gln Ile Gln Lys Phe Met
65                  70                  75                  80

GTG CAG ATC AGC AAG                                                  255
Val Gln Ile Ser Lys
                85

(2) INFORMATION FOR SEQ ID NO: 4:

(i) SEQUENCE CHARACTERISTICS:
        (A) LENGTH: 630 base pairs
        (B) TYPE: nucleic acid
```

(C) STRANDEDNESS: single
        (D) TOPOLOGY: linear (ii) MOLECULE TYPE: cDNA to mRNA (vi) ORIGINAL SOURCE:
        (A) ORGANISM: Homo sapiens
        (F) TISSUE TYPE: epithe cervix of the uteruselial tissues
            in the cervix of ts (ix) FEATURE:
        (A) NAME/KEY: CDS
        (B) LOCATION:1..630
        (C) IDENTIFICATION METHOD: E (xi) SEQUENCE DESCRIPTION: SEQ ID NO: 4:

```
ATG GAG TAT CCC TAT GGA GAG CTC ATC ATC TCC CTG GGC TTC TTT CTT        48
Met Glu Tyr Pro Tyr Gly Glu Leu Ile Ile Ser Leu Gly Phe Phe Leu
 1               5                  10                  15

GTC TTC TTT TTG GAG TCG CTG GCA TTG CAG TGC TGT CCT GGG GCT GCT        96
Val Phe Phe Leu Glu Ser Leu Ala Leu Gln Cys Cys Pro Gly Ala Ala
                20                  25                  30

GGA GGA TCG ACA GTG CAG GAC GAA GAA TGG GGT GGG GCT CAT ATC TTC       144
Gly Gly Ser Thr Val Gln Asp Glu Glu Trp Gly Gly Ala His Ile Phe
            35                  40                  45

GAA CTC CAC AGC CAT GGA CAT TTA CCC TCA CCC TCA AAG GGT CCC CTC       192
Glu Leu His Ser His Gly His Leu Pro Ser Pro Ser Lys Gly Pro Leu
 50                  55                  60

CGA GCC CTT GTC CTC TTG CTG TCA CTC TCC TTT CAC TCA GTG TTT GAA       240
Arg Ala Leu Val Leu Leu Leu Ser Leu Ser Phe His Ser Val Phe Glu
 65                  70                  75                  80

GGG CTA GCT GTG GGG CTG CAG CCG ACA GTA GCA GCT ACC GTG CAG CTC       288
Gly Leu Ala Val Gly Leu Gln Pro Thr Val Ala Ala Thr Val Gln Leu
                85                  90                  95

TGC CTT GCT GTC CTG GCT CAT AAG GGG CTT GTG GTG TTT GGT GTA GGA       336
Cys Leu Ala Val Leu Ala His Lys Gly Leu Val Val Phe Gly Val Gly
                100                 105                 110

ATG CGG CTA GTG CAT TTA GGT ACC AGC TCA CGA TGG GCA GTG TTC TCC       384
Met Arg Leu Val His Leu Gly Thr Ser Ser Arg Trp Ala Val Phe Ser
            115                 120                 125

ATA CTA TTA TTA GCT CTC ATG TCC CCC CTG GGC CTA GCC GTA GGG CTG       432
Ile Leu Leu Leu Ala Leu Met Ser Pro Leu Gly Leu Ala Val Gly Leu
130                 135                 140

GCT GTG ACT GGA GGG GAC TCT GAA GGA GGG CGG GGC TTA GCC CAG GCT       480
Ala Val Thr Gly Gly Asp Ser Glu Gly Gly Arg Gly Leu Ala Gln Ala
145                 150                 155                 160

GTG TTA GAG GGT GTG GCA GCT GGT ACC TTC CTG TAT GTC ACC TTC CTA       528
Val Leu Glu Gly Val Ala Ala Gly Thr Phe Leu Tyr Val Thr Phe Leu
                165                 170                 175

GAA ATT CTT CCA CGG GAG CTA GCT AGT CCT GAG GCC CCT CTA GCT AAG       576
Glu Ile Leu Pro Arg Glu Leu Ala Ser Pro Glu Ala Pro Leu Ala Lys
                180                 185                 190

TGG AGC TGT GTA GCC GCT GGT TTT GCC TTC ATG GCC TTT ATT GCC TTG       624
Trp Ser Cys Val Ala Ala Gly Phe Ala Phe Met Ala Phe Ile Ala Leu
            195                 200                 205

TGG GCC                                                               630
Trp Ala
210
```

(2) INFORMATION FOR SEQ ID NO: 5:

(i) SEQUENCE CHARACTERISTICS:
        (A) LENGTH: 26 amino acids
        (B) TYPE: amino acid

```
            (D) TOPOLOGY: linear (ii) MOLECULE TYPE: peptide (v) FRAGMENT TYPE: internal fragment (xi) SEQUENCE DESCRIPTION: SEQ ID NO: 5:

Thr Ala Glu Ala Leu Glu Glu Ile Glu Ser Gln Ile Gln Lys Phe Met
 1               5                  10                  15

Val Gln Asn Arg Ser Ala Ser Glu Arg Asn
                20                  25

(2) INFORMATION FOR SEQ ID NO: 6:

(i) SEQUENCE CHARACTERISTICS:
         (A) LENGTH: 26 amino acids
         (B) TYPE: amino acid
         (D) TOPOLOGY: linear (ii) MOLECULE TYPE: peptide (v) FRAGMENT TYPE: internal fragment (xi) SEQUENCE DESCRIPTION: SEQ ID NO: 6:

Thr Ala Glu Ala Leu Glu Ser Ile Lys Gln Asp Leu Thr Arg Phe Glu
 1               5                  10                  15

Val Gln Asn Asn His Arg Asn Asn Gln Asn
                20                  25

(2) INFORMATION FOR SEQ ID NO: 7:

(i) SEQUENCE CHARACTERISTICS:
         (A) LENGTH: 26 amino acids
         (B) TYPE: amino acid
         (D) TOPOLOGY: linear (ii) MOLECULE TYPE: peptide (v) FRAGMENT TYPE: internal fragment (xi) SEQUENCE DESCRIPTION: SEQ ID NO: 7:

Phe Gln Glu Ser Cys Glu Ile Ala Glu Thr Glu Val Leu Lys Phe Arg
 1               5                  10                  15

Pro Gln Asn Arg Glu Ala Asp Leu Gln Asn
                20                  25

(2) INFORMATION FOR SEQ ID NO: 8:

(i) SEQUENCE CHARACTERISTICS:
         (A) LENGTH: 26 amino acids
         (B) TYPE: amino acid
         (D) TOPOLOGY: linear (ii) MOLECULE TYPE: peptide (v) FRAGMENT TYPE: internal fragment (xi) SEQUENCE DESCRIPTION: SEQ ID NO: 8:

Thr Ala Glu Gln Leu Glu Glu Leu Glu Arg Ala Phe Glu Arg Thr His
 1               5                  10                  15

Tyr Pro Asp Ile Tyr Thr Arg Glu Glu Leu
                20                  25

(2) INFORMATION FOR SEQ ID NO: 9:

(i) SEQUENCE CHARACTERISTICS:
         (A) LENGTH: 26 amino acids
```

(B) TYPE: amino acid
(D) TOPOLOGY: linear (ii) MOLECULE TYPE: peptide (v) FRAGMENT TYPE: internal fragment (xi) SEQUENCE DESCRIPTION: SEQ ID NO: 9:

```
Thr Ala Glu Gln Leu Glu Glu Leu Glu Lys Ala Phe Glu Arg Thr His
 1               5                  10                  15
Tyr Pro Asp Ile Tyr Thr Arg Glu Glu Leu
            20                  25
```

(2) INFORMATION FOR SEQ ID NO: 10:

(i) SEQUENCE CHARACTERISTICS:
       (A) LENGTH: 309 amino acids
       (B) TYPE: amino acid
       (D) TOPOLOGY: linear (ii) MOLECULE TYPE: peptide (xi) SEQUENCE DESCRIPTION: SEQ ID NO: 10:

```
Met Glu Gln Leu Leu Gly Ile Lys Leu Gly Cys Leu Phe Ala Leu Leu
 1               5                  10                  15
Ala Leu Thr Leu Gly Cys Gly Leu Thr Pro Ile Cys Phe Lys Trp Phe
            20                  25                  30
Gln Ile Asp Ala Ala Arg Gly His His Arg Arg Val Leu Arg Leu Leu
            35                  40                  45
Gly Cys Ile Ser Ala Gly Val Phe Leu Gly Ala Gly Phe Met His Met
        50                  55                  60
Thr Ala Glu Ala Leu Glu Glu Ile Glu Ser Gln Ile Gln Lys Phe Met
65                  70                  75                  80
Val Gln Asn Arg Ser Ala Ser Glu Arg Asn Ser Ser Gly Asp Ala Asp
                85                  90                  95
Ser Ala His Met Glu Tyr Pro Tyr Gly Glu Leu Ile Ile Ser Leu Gly
            100                 105                 110
Phe Phe Leu Val Phe Phe Leu Glu Ser Leu Ala Leu Gln Cys Cys Pro
        115                 120                 125
Gly Ala Ala Gly Gly Ser Thr Val Gln Asp Glu Glu Trp Gly Gly Ala
    130                 135                 140
His Ile Phe Glu Leu His Ser His Gly His Leu Pro Ser Pro Ser Lys
145                 150                 155                 160
Gly Pro Leu Arg Ala Leu Val Leu Leu Ser Leu Ser Phe His Ser
                165                 170                 175
Val Phe Glu Gly Leu Ala Val Gly Leu Gln Pro Thr Val Ala Ala Thr
            180                 185                 190
Val Gln Leu Cys Leu Ala Val Leu Ala His Lys Gly Leu Val Val Phe
        195                 200                 205
Gly Val Gly Met Arg Leu Val His Leu Gly Thr Ser Ser Arg Trp Ala
    210                 215                 220
Val Phe Ser Ile Leu Leu Leu Ala Leu Met Ser Pro Leu Gly Leu Ala
225                 230                 235                 240
Val Gly Leu Ala Val Thr Gly Gly Asp Ser Glu Gly Gly Arg Gly Leu
                245                 250                 255
Ala Gln Ala Val Leu Glu Gly Val Ala Ala Gly Thr Phe Leu Tyr Val
            260                 265                 270
Thr Phe Leu Glu Ile Leu Pro Arg Glu Leu Ala Ser Pro Glu Ala Pro
```

-continued

```
           275                 280                 285
Leu Ala Lys Trp Ser Cys Val Ala Ala Gly Phe Ala Phe Met Ala Phe
   290                 295                 300
Ile Ala Leu Trp Ala
305
```

CELL GROWTH INHIBITOR FACTOR

TECHNICAL FIELD

The present invention relates to a polypeptide useful as an anti-tumor agent having the inhibitory activity on the growth of tumor cells and DNA coding for the polypeptide.

BACKGROUND ART

Cell growth is regulated by balance between the growth promoting mechanism and growth inhibitory mechanism. It is considered that at the time of growth, the promoting mechanism is superior to the inhibitory mechanism, and at the time of growth inhibition, the inhibitory mechanism is superior to the promoting mechanism. In normal cells, this balance is maintained suitably and a typical example is a wound-healing process. For example, if epithelial tissues are damaged, the growth promoting mechanism initiates proliferation and migration of cells to compensate for the damaged site, and when the damaged site is filled up, the growth inhibitory mechanism terminates the growth of the cells. In tumor cells, on the other hand, it is considered that the balance in growth control is lost by abnormal activation of the promoting mechanism or by inactivation of the inhibitory mechanism to permit uncontrollable self-growth of cells. By the advance of recent molecular biology and cell biology, molecules involved in controlling the growth of cells have been revealed, but there are not so many reports on the growth inhibitory and arrest mechanisms as compared with studies on the growth promoting mechanism. Recently, studies on the growth inhibitory mechanisms have been conducted extensively from the viewpoint of controlling cell cycle by tumor-suppression genes, $G_1$ cyclin, cyclin-dependent kinase (CDK), inhibitory factor of CDK etc, but initial stimuli are still not known at the induction of growth arrest.

Known cell growth inhibitory factors having the activity of inhibiting growth of tumor cells include transforming growth factor (TGF)-β which inhibits the growth of lung cancer cells [Proc. Natl. Acad. Sci. USA, 82, 119–123 (1985)] and epidermal growth factor (EGF) which inhibits the growth of squamous carcinoma cells [Nature, 293, 305–307 (1981)].

It is reported that normal tissues from the cervix of the uterus is placed on a culture plate with their epithelial tissues upward, the epithelial cells initiate to grow spread in the form of a sheet around the tissues after 5 to 7 days in the culture [In Vitro Cell. Div. Biol. Animal, 31, 440–446 (1995)]. This sheet of epithelial cells (referred to hereinafter as "outgrowth") has the property of expanding concentrically around normal tissues.

It is known that besides known differentiation marker genes, stress inducible genes, tumor marker genes etc., unknown genes are specifically expressed at the time of growth arrest of outgrowth derived from normal epithelial cells in the cervix of the human uterus [Journal of Stomatological Society of Japan, 62, 78–93 (1995)], but it is not known that specifically expressed unknown genes inhibit the growth of tumor cells.

DISCLOSURE OF THE INVENTION

The present invention relates to a polypeptide consisting of the amino acid sequence of SEQ ID NO: 1 (also referred to hereinafter as ETI-1) or a polypeptide consisting of an amino acid sequence wherein one or more amino acids are deleted, replaced or added in the amino acid sequence of SEQ ID NO:1 and having cell growth inhibitory activity (collectively referred to hereinafter as the polypeptide of the present invention), as well as DNA coding for the polypeptide of the present invention, DNA hybridizing with DNA consisting of the nucleotide sequence of SEQ ID NO:1 or 2, or with an oligonucleotide probe prepared based on said nucleotide sequence (collectively referred to hereinafter as the DNA of the present invention). Further, the present invention relates to a recombinant vector comprising the DNA of the present invention (referred to hereinafter as the recombinant vector of the present invention), a transformant obtained by introducing the recombinant vector of the present invention into host cells (referred to hereinafter as the transformant of the present invention), and a process for producing the polypeptide of the present invention comprising culturing the transformant of the present invention, forming and accumulating the polypeptide of the present invention in a medium, and recovering the polypeptide of the present invention from the culture. Furthermore, the present invention relates to a pharmaceutical composition, preferably an anti-tumor agent, comprising the polypeptide of the present invention as an active ingredient. In addition, the present invention relates to a method of preventing or treating tumor comprising administering an effective amount of the polypeptide of the present invention. Finally, the present invention relates to use of the polypeptide of the present invention for producing a pharmaceutical composition useful for preventing or treating tumor.

Besides the polypeptide consisting of the amino acid sequence shown in SEQ ID NO: 1, the polypeptide of the present invention may be a polypeptide consisting of said amino acid sequence wherein one or more amino acid residues are deleted, replaced or added in the amino acid sequence of SEQ ID NO:1 as long as having cell growth inhibitory activity. Although the number of deleted, replaced or added amino acid residues is not particularly limited, they are preferably one to dozens amino acid residues, particularly one to a few amino acid residues. In addition, it is preferably a polypeptide consisting of an amino acid sequence wherein one or more amino acids residues are deleted, replaced or added in the amino acid sequence of SEQ ID NO:1 so as to have 50% or more, preferably 70% or more, more preferably 90% or more homology to the amino acid sequence of SEQ ID NO: 5 in homology analysis by BCM search launcher [ALIGN analysis using the algorithm of E. Myers and W. Miller, "Optimal Alignments in Linear Space" (CABIOS, 4, 11–17 (1988))].

The polypeptide consisting of the amino acid sequence wherein one or more amino acids are deleted, replaced or added in the amino acid sequence of SEQ ID NO: 1 and having cell growth inhibitory activity includes those polypeptides of SEQ ID NO: 1 where amino acid residue Glu at the 67-, 70-, 73- or 78-position has been replaced by Ala, or a polypeptide consisting of 92 residues where amino acid residues at the 1- to 89-positions are the same as in SEQ ID NO:1 and amino acid residues at the 90 to 92-positions are Lys, Phe and Trp respectively, or a polypeptide consisting of an amino acid sequence as shown in any one of SEQ ID NOS:3 and 5 to 9.

The DNA of the present invention may be any of DNA coding for the polypeptide of the present invention, DNA hybridizing with DNA consisting of a nucleotide sequence as shown in SEQ ID NO: 1 or 2 or with an oligonucleotide probe prepared based on said nucleotide sequence inasmuch as it is DNA coding for a polypeptide having cell growth inhibitory activity.

The DNA of the present invention can be prepared according to the following method.

First, poly(A)+ RNA is separated from epithelial cells producing the polypeptide of the present invention, e.g. outgrowth cells derived from normal human epithelial cells, and cDNA is prepared from said poly(A)+ RNA and integrated into a suitable plasmid vector. Then, the resulting recombinant vector is introduced into host cells to prepare a cDNA library, and clones specifically expressed in growth-arrested cells are selected from the resulting cDNA library, and the above DNA is prepared from the resulting clones.

Specifically, a culture plate just outside (about 0.5 mm from) the edge of outgrowth cells of normal human epithelial cells actively growing concentrically is provided with a deep scratch on the bottom of the plate so as to inhibit the expansion of the cell sheet at the site of the scratch. Poly(A)+ RNA is prepared from the normal human epithelial cells within 7 days, more preferably 2 days after growth was arrested with the scratch made on the culture plate (hereinafter, X days after growth was arrested refers to X days after a culture plate was provided with a scratch), and a cDNA library is prepared using said poly(A)+ RNA.

The epithelial cells producing the polypeptide of the present invention include those derived from ectoderm such as epidermis of skin, mesoderm such as epithelium of peritoneum, and endoderm such as epithelium of intestine, oral cavity or uterine cervix, and preferably used are those derived from endoderm.

The step of preparing a cDNA library by separating poly(A)+ RNA from epithelial cells and the cloning steps can be carried out according to methods described e.g. by Yasutaka Takagi, Gene Manual, Kodansha; Experimental Methods for Gene Manipulation, Kodansha; T. Maniatis et al., Molecular Cloning, Cold Spring Harbor Laboratory (1982); T. Maniatis, et al., Molecular Cloning, $2^{nd}$ ed., Cold Spring Harbor Laboratory (1989) etc.

Process to select cDNA clones specifically expressed in growth-terminated outgrowth cells from the cDNA library includes methods using conventional differential hybridization such as colony hybridization, DNA dot blotting, RNA slot blotting etc., besides subtraction cloning [e.g. a method described in Biochem. Biophysic. Res. Commu., 185, 1155–1161 (1992)] used widely for cloning cDNA from tissue-specifically expressed poly(A)+ RNA. To confirm that the cDNA clones thus selected are the DNA of the present invention, a DNA fragment containing said cDNA is prepared and then integrated into a vector used for introducing a gene into animal cells such as human and the resulting recombinant vector is introduced into tumor cells to determine whether the growth of the tumor cells is inhibited by introducing the recombinant vector.

The tumor cells include cells such as retinoblastoma, neurofibroma, osteosarcoma, breast cancer, lung cancer, bladder cancer, glioblastoma, uterine cancer, ovarian cancer etc. or cell strains derived from these cells.

The cDNA clones selected in the above method are cleaved with suitable restriction enzymes such as PstI etc. and cloned in plasmids such as pBluescript KS(+) (Stratagene), and then analyzed using a conventional nucleotide sequence analysis method, e.g. the dideoxy method of Sanger et al. [Proc. Natl. Acad. Sci., USA, 74, 5463 (1977)] etc. whereby the nucleotide sequence of said gene can be determined. The analysis of the nucleotide sequence can be performed using a nucleotide sequence automatic analyzer, e.g. 373A DNA Sequencer (Applied Biosystems) etc.

The nucleotide sequence thus determined includes e.g. the nucleotide sequence of SEQ ID NO:2. The DNA consisting of the nucleotide sequence of SEQ ID NO:2 contains a nucleotide sequence consisting of 927 nucleotides at the 131- to 1057-positions as a region coding for the polypeptide of the present invention, that is, the nucleotide sequence of SEQ ID NO:1.

Once the nucleotide sequence of SEQ ID NO:1 or 2 is determined, the DNA of the present invention can be obtained by chemical synthesis or PCR (polymerase chain reaction) using DNA consisting of said nucleotide sequence as a template.

DNA consisting of the nucleotide sequence of SEQ ID NO:1 or 2 is cleaved with restriction enzyme NdeI or subjected to site-directed mutagenesis [Genetic Engineering, 3, 1–32, Plenum Press, New York (1981), Nucleic Acid Research, 10, 6487–6500 (1982), Gene, 77, 51–59 (1989) etc.] so that the DNA of the present invention can be obtained as DNA coding for a polypeptide consisting of the amino acid sequence in which one or more amino acids are deleted, replaced or added in the amino acid sequence of SEQ ID NO:1 and having cell growth inhibitory activity.

The DNA of the present invention can also be obtained as DNA which in a solution containing e.g. 50% formamide, 5×SSPE, 5×Denhalt solution, 0.5% SDS, 100 μg/ml salmon sperm DNA at 42° C. for 16 hours, hybridizes with a labeled DNA probe in which DNA consisting of the nucleotide sequence of SEQ ID NO:1 or 2 or an oligonucleotide probe prepared based on said nucleotide sequence has been labeled with a radioisotope, biotin etc.

The DNA of the present invention can be used in a recombinant vector and as a DNA probe to diagnose cancer etc.

After a DNA fragment containing the DNA of the present invention was prepared with restriction enzymes etc., the recombinant vector of the present invention can be prepared by inserting said DNA fragment into a downstream region of a promoter in an expression vector.

The transformant of the present invention is obtained by introducing the recombinant vector of the present invention into host cells compatible with the expression vector used in constructing said vector.

Any host cells capable of expressing the target gene can be used. Examples of such host cells are microorganisms belonging to the genera Escherichia, Serratia, Bacillus, Brevibacterium, Corynebacterium, Pseudomonas, Microbacterium etc. such as *Escherichia coli, Bacillus subtilis, Bacillus amyloliquefacines, Brevibacterium flavum, Brevibacterium lactofermentum, Corynebacterium glutamicum, Microbacterium ammoniaphilum*, yeasts such as *Saccharomyces cerevisae, Schizosaccharomyces pombe, Kluyveromyces lactis, Trichosporon pullulans, Schwanniomyces alluvius* etc., animal cells such as namalwa cells, COS cells, CHO cells etc.

The expression vector preferably includes those being capable of autonomous replication in the host cells or capable of integration in the chromosome and containing a promoter at a region permitting transcription of the polypeptide of the present invention.

To use microorganisms such as *E. coli* as host cells, the recombinant vector of the present invention is preferably one being capable of autonomous replication in said microorganisms and being composed of a promoter, a ribosome-binding sequence, the DNA of the present invention and a transcription termination sequence. A gene controlling the promoter may be contained in it.

The expression vector includes e.g. pBTrp2, pBTac1, pBTac2 (all of which are available from Boehringer Mannheim), pKYP200 [Agric. Biol. Chem., 48, 669–675 (1984)], PLSA1 [Agric. Biol. Chem., 5, 277 (1989)], pGEL1 [Proc. Natl. Acad. Sci., USA, 82, 4306 (1985)], pBluescript (Stratagene) etc.

The promoter may be any one which is capable of expression in host cells such as $E.$ $coli$ etc. For example, promoters derived from $E.$ $coli$, phage etc., such as trp promoter (Ptrp), lac promoter (Plac), $P_L$ promoter and $P_R$ promoter are used. Promoters having 2 Ptrp connected in series (Ptrp×2), artificially designed and modified promoters such as tac promoter etc, may be used.

The ribosome-binding sequence may be any one which is capable of expression in host cells such as $E.$ $coli$ etc. Preferably, the ribosome-binding sequence is regulated such that it is apart at a suitable distance (e.g. 6 to 18 nucleotides) from the initiation codon.

It is preferred in the recombinant vector of the present invention that some nucleotides in the DNA of the present invention are replaced as necessary so that the optimum codon for expression in host cells can be attained.

In the recombinant vector of the present invention, the transcription termination sequence is not necessarily required for expression of the DNA of the present invention, but the transcription termination sequence is preferably located just downstream from the structural gene.

The method of introducing the recombinant vector into microorganisms may be any method of introducing DNA into microorganisms, and examples include a method using calcium ion [Proc. Natl. Acad. Sci., USA, 69, 2110–2114 (1972)], the protoplast method (Japanese Patent Appln. LOP Publication No. 2483942/88) etc.

In cases where yeast is used as host cells, expression vectors such as YEp13 (ATCC37115), YEp24 (ATCC37051), YCp50 (ATCC37419) etc. are used.

The promoter may be any one which is capable of expression in yeast. Examples include a promoter for genes of hexokinase etc. in the glycolytic pathway, gal 1 promoter, gal 10 promoter, heat shock protein promoter, MF α1 promoter, CUP 1 promoter etc.

The method of introducing the recombinant vector into yeast may be any method of introducing DNA into yeast. Examples include the electroporation method [Methods. Enzymol., 194, 182–187 (1990)], the spheroplast method [Proc. Natl. Acad. Sci., USA, 84, 1929–1933 (1978)], the lithium acetate method [J. Bacteriol. 153,163–168 (1983)] etc.

In cases where animal cells are used as host cells, expression vectors such as pcDNAI/Amp, pcDNAI, pCDM8 (all of which are available from Invitrogen) etc. are used. In this case, any promoters which is capable of expression in an animal cell, for example, a promoter for IE (immediate early) gene from human CMV, etc., may be used. Further, an enhancer for IE gene from human CMV may be used along with the promoter.

The method of introducing the recombinant vector into animal cells may be any method of introducing DNA into animal cells. Examples include the electroporation method [Cytotechnology, 3, 133 (1990)], the calcium phosphate method (Japanese Patent Appln. LOP Publication No. 227075/90), the lipofection method [Proc. Natl. Acad. Sci. USA, 84, 7413 (1987)] etc.

The polypeptide of the present invention can be produced by culturing the transformant of the present invention in a medium, then forming and accumulating the polypeptide of the present invention in the culture, and recovering said polypeptide from the culture.

The method of culturing the transformant of the present invention in a medium is carried out according to a conventional method used for culturing the host cells.

The medium for culturing the transformant obtained from microorganisms such as $E.$ $coli$, yeast etc. as hosts may be any natural or synthetic mediums containing a carbon source, a nitrogen source, inorganic salts etc. which the microorganisms can assimilate and in which the transformant can be cultured efficiently.

The carbon source includes carbohydrates such as glucose, fructose, sucrose, molasses, starch, starch hydrolysate, organic acids such as acetic acid, propionic acid etc., and alcohols such as ethanol, propanol etc.

The nitrogen source includes ammonia, ammonium salts of inorganic or organic acids, such as ammonium chloride, ammonium sulfate, ammonium acetate, ammonium phosphate etc. or any other nitrogen-containing compounds, peptone, meat extract, yeast extract, corn steep liquor, casein hydrolysate, soybean cake and soybean cake hydrolysate, various kinds of fermentative bacteria or digests thereof etc.

The inorganic matter includes e.g. potassium dihydrogen phosphate, potassium phosphate, magnesium phosphate, magnesium sulfate, sodium chloride, ferrous sulfate, manganese sulfate, copper sulfate, calcium carbonate etc.

Culture is carried out under aerobic conditions normal shake culture or submerged shake culture under aeration at 15 to 40° C. for 16 to 96 hours. During culturing, pH is maintained in the range of 3.0 to 9.0. pH adjustment is carried out using inorganic or organic acid, alkaline solution, urea, calcium carbonate, ammonia etc.

During culturing, antibiotics such as ampicillin, tetracycline etc. may be added to the medium.

When a microorganism transformed with the expression vector whose promoter is an inducible promoter is cultured, an inducer may be added as necessary to the medium. For example, when a microorganism transformed with the expression vector using the lac promoter is cultured, isopropyl-β-D-thiogalactopyranoside (IPTG) etc. may be added to the medium, and when a microorganism transformed with the expression vector using the trp promoter is cultured, indoleacrylic acid (IAA) etc. may be added.

The medium for culturing the resulting transformant from animal cells as host includes a generally used RPMI 1640 medium, Eagle's MEM medium etc. optionally containing fetal bovine serum etc.

Culture is usually carried out in 5% $CO_2$ at 35 to 37° C. for 3 to 7 days.

During culturing, antibiotics such as kanamycin, penicillin etc. may be added to the medium.

After culturing, if the polypeptide of the present invention is produced in the microorganism or cells, the polypeptide is extracted from the microorganism or cells by, for example, disruption of, and if the polypeptide of the present invention is excreted from the microorganism or cells, after removal of the microorganism or cells by, for example, centrifugation, the polypeptide can be isolated and purified directly from the culture by general biochemical methods used in protein isolation and purification, such as sulfate ammonium precipitation, gel filtration, ion-exchange chromatography, affinity chromatography, etc.

The polypeptide of the present invention is orally or parenterally administered as such or in forms of various pharmaceutical compositions. The forms of such pharmaceutical compositions include e.g. tablets, pills, powder, granules, capsules, suppositories, injections, infusions etc.

To manufacture such forms of pharmaceutical compositions, conventionally known methods can be applied and e.g. various excipients, lubricants, binders, disintegrating agents, suspending agents, isotonic agent, emulsifier, absorption promoter, stabilizer etc. may be contained.

The carriers used in the pharmaceutical composition includes e.g. water, distilled water for injection, saline, glucose, fructose, white sugar, mannitol, lactose, starch, corn starch, cellulose, methylcellulose, carboxymethylcellulose, hydroxypropylcellulose, alginic acid, talc, sodium citrate, calcium carbonate, calcium hydrogen phosphate, magnesium stearate, urea, silicone resin, sorbitan fatty ester, glycerin fatty ester, etc., and these are suitably selected depending on the type of the pharmaceutical composition.

Although the dosage and frequency of administration vary depending on the desired therapeutic effect, administration method, period of therapy, age, weight etc., it is administered preferably orally or parenterally (e.g. by injection, infusion, rectum administration using a suppository, skin attachment etc.) usually at a dose of 0.01 to 2 mg/kg per a day for an adult.

Hereinafter, the present invention is described in more detail by reference to Examples. However, the present invention is not limited to these Examples.

BEST MODE FOR CARRYING OUT THE INVENTION

EXAMPLE 1

Outgrowth Cell Culture of Normal Human Epithelial Cells

Normal tissues of the uterine cervix were excised from surgical specimens of hysteromyoma patients, and their interstitial parts were removed as thoroughly as possible. The tissues were washed 3 times with Dulbecco's modified Eagle's medium (DME medium, Kyokuto Seiyaku K.K.) containing 4 µg/ml Fungizone (Gibco) and 1% fetal bovine serum (FBS, Bocknek). The washed tissues were cut into about 2 to 4 mm² pieces to prepare tissue fragments. To improve adhesion of the explants, the surface of a culture plate was scratched with a short needle, and the culture plate was coated with HEPES buffered saline (HBS) containing 10 µg/ml human fibronectin, 30 µg/ml collagen type I (Nitta Gelatin) and 100 µg/ml bovine serum albumin (Sigma). The tissue fragments were placed at the scratched site of the culture plate with the epithelial surface upside and the interstitial part downside, and the tissues were left at room temperature for 1 hour and then cultured at 37° C. in 5% $CO_2$ in DMMC medium containing 4% FBS whereby outgrowth of the normal human epithelial cells were obtained. The DMMC medium is a medium containing DME medium and MCDB153 HAA medium (MCDB medium, Kyokuto Seiyaku) in equal amounts where phenol red and growth factor were removed and $Ca^{2+}$ concentration was adjusted to 0.9 mM. The DMMC medium contains 1 µg/ml Fungizone, 100 U/ml penicillin (Meiji Seika) and 50 µg/ml gentamicin (Sigma) as antibiotics. The medium was exchanged with fresh one every other day.

EXAMPLE 2

Preparation of cDNA Library From Growth-arrested Normal Human Epithelial Cells

The outgrowth cells of normal human epithelial cells obtained in Example 1 were placed on a culture plate and allowed to actively grow concentrically, and the culture plate was provided at the bottom with a deep groove just outside (about 0.5 mm from) the edge of a cell sheet of outgrowth cells to inhibit the spread of the cell sheet at the site of the groove.

Using Fast Track mRNA Isolation Kit (Invitrogen), poly (A)$^+$ RNA was prepared from the outgrowth cells of normal human epithelial cells 2 days after growth was arrested (referred to hereinafter as growth-arrested epithelial cells). cDNA was synthesized from 5 µg of the resulting poly(A)$^+$ RNA using Super Script RT (BRL) where an oligo(T)n fused with an XhoI cleavage sequence was used as a primer. The subsequent procedure was carried out essentially using Zap-cDNA Synthesis Kit (Stratagene). The single-stranded cDNA thus synthesized was converted into a double-stranded form by reaction with DNA polymerase I and RNAase H at 16° C. for 150 minutes. Then, the double-stranded fragment was blunt-ended by reaction with T4 DNA polymerase at 37° C. for 30 minutes and then reacted with T4 DNA ligase at 4° C. for 24 hours whereby EcoRI adaptors were ligated respectively to both ends of the chain. After treatment at 70° C. for 30 minutes, it was reacted with T4 polynucleotide kinase at 37° C. for 30 minutes and then at 70° C. for 30 minutes so that the EcoRI cleavage ends were phosphorylated, and further digestion was carried out by reaction with XhoI at 37° C. for 30 minutes. The resulting cDNA insert with XhoI and EcoRI cleaved ends at both ends was ligated to an XhoI/EcoRI site of UNI-Zap XR vector (Stratagene) by reaction with T4 DNA ligase at 4° C. for 48 hours, and then packaged into λ phage particles by use of GIGAPACK II (Stratagene). *E. coli* SURE (Stratagene) was infected with this λ phage and amplified to prepare a phage library. The titer of the resulting library was $9.4 \times 10^5$ pfu/µg arm and the average length of the inserts was 1.7 kbp.

EXAMPLE 3

Subtraction Screening

Using helper phages ExAssist and VCSM13 (f1) (Stratagene), the phage clones of the cDNA library from growth-arrested epithelial cells were converted into antisense single-stranded DNA. Fifteen µg poly(A)$^+$ RNA prepared using Fast Track MRNA isolation kit (Invitrogen) from actively growing outgrowth cells of normal human epithelial cells (referred to hereinafter as growing epithelial cells) was mixed with an equal volume of long-arm photoprobe biotin (Vector) and exposed to light for 15 minutes. After further addition of a half-volume of long-arm photoprobe biotin, the sample was exposed to light for 15 minutes whereby poly(A)$^+$ RNA was labeled with biotin. Fifteen µg of the biotin-labeled poly(A)$^+$ RNA obtained from the growing epithelial cells was mixed with 1 µg of the antisense single-stranded DNA prepared from the cDNA library from growth-arrested epithelial cells obtained in Example 2 and then dissolved in 50 µl Berk Sharp hybridization buffer and heated at 65° C. for 10 minutes, and hybridization was carried out at 40° C. for 48 hours. After reaction, 40 µl HEPES-EDTA solution (10 mM HEPES, 1 mM EDTA) was added to the reaction solution, and nucleic acid was precipitated with ethanol. The precipitated nucleic acid was dissolved again in 340 µl HEPES-EDTA solution, and the operation of removing the biotin-labeled nucleic acid (RNA or RNA/DNA hybrid) by adsorption onto streptoavidin agarose (Pharmacia) was carried out twice. The DNA remaining in the solution was precipitated with ethanol, and 5 µg of biotin-labeled poly(A)$^+$ RNA from growing epithelial cells was added, and subtraction hybridization was carried out again under the same conditions as above. Single-stranded DNA remaining after the repeated subtraction screening was converted into a double-stranded chain DNA by reaction at 70° C. for 20 minutes with M13 reverse sequencing primer (Promega) as DNA specific to the growth-arrested epithelial cells in the presence of Vent DNA polymerase (NEB), followed by extraction with phenol/chloroform. The resulting double-stranded DNA was purified using GENE CLEAN (BIO 101) and introduced by the electroporation method into *E. coli* Electromax DH10B (BRL) to give clones.

EXAMPLE 4

Screening by Differential Hybridization

1) Colony Hybridization $6.7 \times 10^4$ clones obtained by subtraction screening in Example 3 were plated on six 150-mm plates and cultured at 37° C. overnight and left at 4° C. for 1 day. The colonies were transferred to 2 sheets of nitrocellulose filter (S&S) and washed with 0.5 N sodium hydroxide for 5 minutes, then with 1 M Tris-HCl, pH 8.0 for 5 minutes, 1 M Tris-HCl, pH 8.0 containing 1.5 M sodium chloride for 5 minutes, and 2×SSC (sodium citrate-sodium chloride) for 5 minutes and then exposed to ultraviolet rays for cross-linking. The filter with the DNA fixed on it was then treated with 1×SSC containing 0.2% SDS and 50 µg/ml proteinase K at 55° C. for 30 minutes and then washed with 2×SSC at room temperature twice. DNA probes were prepared using 2 µg each of poly(A)$^+$ RNA prepared respectively from growing epithelial cells and growth-arrested epithelial cells and [$\alpha$-$^{32}$p] dCTP (Amersham) using Super Script RT (BRL), and the filter was subjected to pre-hybridization at 42° C. for 3 hours and hybridization at 42° C. for 16 hours in a solution consisting of 50% formamide, 5×SSPE, 5×Denhalt solution, 0.5% SDS and 100 µg g/ml salmon sperm DNA. The cDNA probes were prepared using BcaBEST Labeling Kit (Takara Shuzo) and [$\alpha$-$^{32}$P] dCTP (Amersham). After hybridization, the filter was washed twice with 2×SSPE containing 0.1% SDS at room temperature for 10 minutes, once with 1×SSPE containing 0.1% SDS at 65° C. for 15 minutes, and twice with 0.1×SSPE containing 0.1% SDS at 65° C. for 10 minutes. Then, it was subjected to autoradiography. As a result of autoradiography, colonies hybridizing better with the cDNA probe derived from growth-arrested epithelial cells were selected. Secondary screening was carried out under the same conditions. The selected colonies were placed respectively on a 96-well micro-titer plate with LB medium containing 100 µg/ml ampicillin and then cultured, and glycerol was added if necessary, and they were stored at −80° C.

2) DNA Dot Blotting

The clones obtained by colony hybridization were inoculated onto a 96-well micro-titer plate containing 200 µl liquid medium per well and cultured at 37° C. overnight. 100 µl of the culture medium was transferred to a new 96-well micro-titer plate, and aq. sodium hydroxide was added thereto at a final concentration of 0.3 N and the sample was treated at room temperature for 5 minutes, followed by adding an equal volume of 2 M ammonium acetate. The resulting solution was dot-blotted onto a nitrocellulose filter in an amount of 20 µl for each dot and washed with 1 M ag. ammonium acetate and fixed on the filter by exposure to ultraviolet rays. Construction of a cDNA probe and hybridization were carried out using the same procedures as in colony hybridization, and then autoradiography was carried out. Based on the result of autoradiography, colonies hybridizing better with the cDNA probe derived from growth-arrested epithelial cells were selected.

3) RNA Slot Blotting

Using slot blotting (Bio Rad), 50 ng/slot each of poly (A)$^+$ RNAs derived respectively from growing epithelial cells and growth-arrested epithelial cells was blotted onto a Hybond-N nylon membrane (Amersham) and fixed on the membrane by exposure to ultraviolet rays. The clones selected by colony hybridization and DNA dot blotting were labeled with [$\alpha$-$^{32}$p] dCTP (Amersham) using BcaBEST Labeling Kit and used as DNA probe, and hybridization was carried out using the same procedures as in colony hybridization, and autoradiography was then carried out. Based on the results of autoradiography, cDNA clones which were highly expressed at the time of growth arrest were selected.

EXAMPLE 5

Sequencing of cDNA

Single-stranded DNA of pBluescript SK (−) containing the cDNA clones highly expressed at the time of growth arrest obtained in Example 4 was prepared using M13 helper phage, and its nucleotide sequence of 200 to 300 bp or thereabout from the 5'-terminal was determined using SEQUENASE DNA Sequencing Kit (USB), T3 primer, universal primer and synthetic oligonucleotide primer. The determined nucleotide sequence was subjected to homology search using GCG program [J. Mol. Biol., 215, 403–410 (1990)].

EXAMPLE 6

Northern Blotting

As a result of the homology search in Example 5, one of clones containing a cDNA insert of unknown nucleotide sequence was designated *Escherichia coli* (*E. coli*) 6A1. This strain has been deposited under the Budapest Treaty as FERM BP-5476 since March 15, 1996 with the National Institute of Bioscience and Human-Technology [1–3, Higashi 1-chome, Tsukuba-shi, Ibaraki-ken, Zip Code 305], Agency of Industrial Science and Technology, the Ministry of International Trade and Industry, Japan, Using Fast Track MRNA Isolation Kit, a poly (A)$^+$ RNA solution was prepared from growth-arrested epithelial cells. To 5 µl of the prepared solution (1 µg/µl) were added 2 µl of 5×formaldehyde gel-running buffer [0.1 M MOPS, 40 mM sodium acetate, 5 mM EDTA (pH 7.0)], 3.5 µl formaldehyde and 10 µl formamide. After the mixture was heated at 65° C. for 15 minutes, 2 µl formaldehyde gel-loading buffer [50% glycerol, 1 mM EDTA, 0.25% Bromophenol Blue, 0.25% Xylenecyanol FF (pH 7.0)] was added to it, and the sample was electrophoresed at 100 V. After electrophoresis, the RNA was transferred by capillary transfer from the gel to a Hybond-N nylon membrane (Amersham) and fixed on the membrane by exposure to ultraviolet rays. Construction of a probe and hybridization were carried out using the same manner as in RNA slot hybridization, and autoradiography was then carried out. Based on the results of autoradiography, the cDNA probe prepared from *E. coli* 6A1 was shown to hybridize specifically with about 1.3 kb poly(A)$^+$ RNA from growth-arrested epithelial cells.

EXAMPLE 7

Sequencing of the Full-length cDNA pBluescript SK (−) containing the cDNA prepared from *E. coli* 6A1 was denatured by heating at 37° C. for 30 minutes in an aqueous solution containing 0.2 M sodium hydroxide and 0.2 mM EDTA, and the nucleotide sequence of the cDNA was determined using SEQUENASE DNA Sequencing Kit (USB) and T3 primer. Said cDNA was digested with Kpn I and Sac I, and the resulting fragment was sub-cloned into pBluescript SK(+) and pBluescript SK(−) and then made single-stranded with M13 helper phage, and the nucleotide sequence (SEQ ID NO:2) containing the cDNA coding for the full length polypeptide was determined using SEQUENASE DNA Sequencing Kit, T3 primer, universal primer and synthetic oligonucleotide primer.

The length of the nucleotide sequence as shown in SEQ ID NO:2 excluding poly(A)$^+$ tail was 1356 bp and nearly agreed with the result of Northern blotting in Example 6. The open reading frame in this cDNA consisted of 927 bp from nucleotide 131 to nucleotide 1057 in the nucleotide sequence shown in SEQ ID NO:2 and coded for 309 amino acids, and the theoretical molecular weight of a protein translated therefrom is 34 Kd. The sequence around ATG codon as a translation initiation site agreed with the sequence of the translation initiation site proposed by Kozak [Cell, 44, 283–292 (1986)]. PolyA signal (AATAAA) was located upstream by 27 nucleotides from the first A in poly(A)$^+$ tail. In addition, the sequence (ATTTA) involved in instability of MRNA was located at three positions in the 3'-untranslated region.

The amino acid sequence as shown in SEQ ID NO: 1 (polypeptide-coding region in the nucleotide sequence as shown in SEQ ID NO:2) has hydrophobic regions widely. An amino acid sequence of from the 70- to 104-positions in the amino acid sequence shown in SEQ ID NO: 1 forms a hydrophilic region with hydrophobic amino acids at both ends, and in this region, there are two N-glycosylation sites at the 83- and 90-positions respectively and one site at the 92- to 93-positions (Ser-Gly) to which glycosaminoglycan may bind.

To confirm the nucleotide sequence shown in SEQ ID NO: 2, a clone hybridizing with the nucleotide sequence shown in SEQ ID NO: 2 was selected in the same manner as in colony hybridization except that DNA consisting of the full-length nucleotide sequence shown in SEQ ID NO: 2 was hybridized as a DNA probe with the cDNA library obtained in Example 2. The nucleotide sequence of the selected clone was determined in the same manner as above. As a result, it was found that there are cDNA clones whose polypeptide-coding region is the nucleotide sequence as shown in SEQ ID NO:3. DNA consisting of the nucleotide sequence as shown in SEQ ID NO: 3 is deficient in 5 bp of nucleotides 377 to 381 in the nucleotide sequence shown in SEQ ID NO: 2. As a result, a frame shift occurred in the following sequence and a polypeptide consisting of the amino acid sequence shown in SEQ ID NO: 3 was a polypeptide consisting of 85 residues, and its amino acid sequence of from N-terminal to residue 82 was the same as the amino acid sequence shown in SEQ ID NO: 1. It was confirmed by the RT-PCR method [J. Immunol., 153, 981–987 (1991)] that the nucleotide sequences shown in SEQ ID NOS:1 and 3 are produced as transcription products in normal human epithelial cells.

EXAMPLE 8

Result of Data Base Search

As a result of data base search using GCG program, no significant homology of the nucleotide sequence and amino acid sequence shown in SEQ ID NOS:1 and 2 to known ones was found.

However, when the full length amino acid sequence shown in SEQ ID NO:1 was subjected to data base search [Genome Research, 5, 173–184 (1995)] using a program named BEAUTY from Human Genome Center, Bayler College of Medicine, Houston Tex., the amino acid sequence (SEQ ID NO:5) of from the 65- to 90-positions in the amino acid sequence shown in SEQ ID NO:1 had homology to the amino acid sequence (SEQ ID NO:6) of from the 17- to 42-positions in a polypeptide consisting of 1099 residues obtained by expressing tumor-suppressor gene Warts from Drosophila [Genes Dev., 9, 534–546 (1995)]. Because the amino acid sequence of from the 65- to 90-positions in the amino acid sequence shown in SEQ ID NO: 1 forms a hydrophilic region, it was assumed that this region is very likely to be exposed to the outside of the protein, thus acting as a functional domain. Accordingly, an amino acid sequence of 30 to 50 residues containing its neighboring region was examined using the same data base. As a result, it was shown to have homology to: an amino acid sequence (SEQ ID NO: 7) of from the 707- to 732-positions in a polypeptide consisting of 741 residues obtained by expressing Xenopus XPMC1 gene [Gene, 145, 155–6 (1994)] complementing abnormal division of yeast; an amino acid sequence (SEQ ID NO:8) of from the 227- to 252-positions in a polypeptide consisting of 479 residues obtained by expressing paired domain-containing mouse Pax-3 gene [EMBO J., 10, 1135–1147 (1991)]; and an amino acid sequence (SEQ ID NO:9) of from the 189- to 214-positions in a polypeptide consisting of 290 residues obtained by expressing paired domain-containing mouse Pax-7 gene [Mech. Dev., 33, 27–37 (1990)]. These polypeptides obtained by expressing the 4 genes do not have high homology to one another as a whole, but their partial amino acid sequences in the above regions have high homology to one another (homology of the amino acid sequence of SEQ ID NO: 5 to the amino acid sequences of SEQ ID NOS: 6, 7, 8 and 9 are 77%, 62%, 57% and 62% respectively). Further, any of these 4 genes are estimated to participate in growth regulation of cells.

EXAMPLE 9

In Vitro Transcription and Translation pBluescript SK (−) containing cDNA with the nucleotide sequence shown in SEQ ID NO: 2 was made linear DNA by digestion with Xho I. T3 RNA polymerase (Ambion) was reacted with this linear DNA as a template at 37° C. for 3 hours to prepare RNA, and the template DNA was digested with 2 U of DNase I at 37° C. for 15 minutes. The prepared RNA was added to wheat germs extract (Promega) containing [$^{35}$S]-methionine (Amersham) and translated into a protein by reaction at 25° C. for 1 hour. The resulting protein was electrophoresed on 15% polyacrylamide gel at 150 V. After electrophoresis, the gel was fixed by immersion in 7% acetic acid for 5 minutes, washed with de-ionized water, treated with Amplify (Amersham), dried and subjected to autoradiography.

As a result, a single band was confirmed in a position corresponding to 34 kd which is a theoretical molecular weight of the polypeptide obtained by translation of the nucleotide sequence.

EXAMPLE 10

Evaluation of Activity (1)

1) Preparation of Expression Vectors

A DNA fragment coding for the full-length coding region of the nucleotide sequence shown in SEQ ID NO: 1

(polypeptide consisting of 309 residues), a DNA fragment consisting of the nucleotide sequence shown in SEQ ID NO: 3 (coding for a polypeptide consisting of 85 residues containing 82 residues starting from the N-terminal in SEQ ID NO: 1) and a DNA fragment consisting of the nucleotide sequence shown in SEQ ID NO: 4 (coding for a polypeptide consisting of 210 residues starting from the C-terminal in SEQ ID NO:1) were amplified by PCR using a cDNA fragment with the nucleotide sequence shown in SEQ ID NO: 2. Then, these DNA fragments were integrated into PCR cloning vector pCR2 (Invitrogen). The resulting recombinant plasmid was introduced into *E. coli* INV αF' and the transformant was selected as an ampicillin-resistant strain, and PCR cloning vectors p38, p8 and p28 were prepared respectively.

p38, p8 and p28 were cleaved at the EcoRI site of pCR2 and separated by 2% agarose gel electrophoresis, and DNA fragments coding for the above polypeptides were isolated using GENE CLEAN II (BIO 101). Each of the resulting DNA fragments was ligated with a ligation kit (Takara Shuzo) to human animal cell expression vector pcDNA3 (Invitrogen) cleaved with EcoRI. Each of the resulting human animal cell expression vectors was introduced into XL-1 blue MRF', and each transformant was cultured in TB medium containing ampicillin and each plasmid was recovered using a plasmid kit (Qiagen). Among the prepared human animal cell expression vectors, those having the expression DNA insert in the sense direction to the CMV promoter on pcDNA3 were designated p38, p8 and p28 respectively, and those having it in the anti-sense direction were designated p38A, p8A and p28A respectively.

2) Transfection $4\times10^5$ cells from cell strain SiHa derived from squamous carcinoma cells in the cervix of the uterus (obtained from Cell Bank, Human Science Shinko Zaidan, Japan) were inoculated onto a culture plate of 60 mm in diameter with DME medium containing 10% FBS and cultured at 37° C. overnight. The resulting cell strain was transfected with human animal cell expression vectors p38, p8, p28, p38A, p8A, p28A and pCDNA3 by the lipofection method [Proc. Natl. Acad. Sci., USA, 84, 7413 (1987)] to prepare gene-introduced strains 325s, 221s, 936s, 325a, 221a, 936a and SiHa-C respectively. As the reagent for introducing the DNA, lipofectamine or lipofectin (Gibco) was used.

3) Measurement of Growth Inhibitory Activity i) In cases where cells were less damaged upon transfection and cells grew, the cells were cultured 2 days after transfection, and a calcium- and magnesium-free PBS medium containing 0.25% trypsin and 0.02% EDTA was added to the culture plate, and the cells were treated at 37° C., for 10 minutes and then recovered. The recovered cells were inoculated respectively into 2 culture plates of 60 mm in diameter with DME medium containing 1 mg/ml G418 (neomycin, Gibco) and 10% FBS respectively and cultured for 14 days.

ii) In cases where cells were highly damaged upon transfection and nearly all cells perished, G418 was added to the medium and cultured for 10 days.

After culturing was finished in i) and ii) above, the resulting colonies were fixed in PBS containing 10% formalin at room temperature for 30 minutes and stained with 0.1% aq. Crystal Violet at room temperature for 10 minutes, and the number of stained colonies was counted. The results are shown in Table 1.

TABLE 1

| Gene-introduced strain (Human animal cell expression vector) | Number of stained colonies (stained colonies/total colonies) | |
|---|---|---|
| | i) Day 10 | ii) Day 14 |
| 325s (p38) | 29 (16%) | 69 (34%) |
| 221s (p8) | 134 (72%) | 189 (93%) |
| 936s (p28) | 147 (79%) | 172 (85%) |
| 325a (p38A) | 168 (90%) | 212 (104%) |
| 221a (p8A) | 199 (106%) | 190 (94%) |
| 936a (p28A) | 147 (79%) | 194 (96%) |
| SiHa-C (pcDNA3) | 187 (100%) | 203 (100%) |

As shown in Table 1, gene-introduced strain 325s (SiHa transfected with p38) only was observed to have cell growth inhibitory effect.

EXAMPLE 11

Evaluation of Activity (2)

1) Preparation of Expression Vectors

Human animal cell expression vectors p38, p8 and p28, p38A, p8A and p28A were prepared respectively in the same manner as in Example 10 1).

2) Transfection $3\times10^5$ epithelial cell strain Vero cells derived from the kidney of African green monkey (Cercopithecus sabaeus) (obtained from Cell Bank, Human Science Shinko Zaidan) were inoculated into a culture plate of 60 mm in diameter with EME medium containing 10% FBS and incubated at 37° C. overnight. Using the lipofection method [Proc. Natl. Acad. Sci. USA, 84, 7413 (1987)], the resulting cell strain was transfected with human animal cell expression vectors p38, p8, p28, p38A, p8A, p28A and pCDNA3 obtained in 1) above whereby gene-introduced strains 325S, 221S, 936S, 325A, 221A, 936A and PCDNA3 were prepared respectively.

3) Measurement of Growth Inhibitory Activity

After the cells were cultured for 2 days after transfection, a calcium- and magnesium-free PBS medium containing 0.25% trypsin and 0.02% EDTA was added to the culture plate, and the cells were treated at 37° C. for 5 minutes and then recovered. The recovered cells were plated at a 1:1:4:4 ratio in the number of cells onto 4 culture plates of 100 mm in diameter with EME medium containing 1 mg/ml G418 and 10% FBS, and then cultured for 10 days. After culturing, the resulting colonies were fixed in PBS containing 10% formalin at room temperature for 30 minutes and stained with 0.1% aq. Crystal Violet at room temperature for 10 minutes, and the number of stained colonies was counted. The results are shown in Table 2.

TABLE 2

| Gene-introduced strain (Human animal cell expression vector) | Number of stained colonies (stained colonies/total colonies) |
|---|---|
| 325S (p38) | 15 (2%) |
| 221S (p8) | 70 (6%) |
| 936S (p28) | 550 (46%) |
| 325A (p38A) | 1092 (91%) |
| 221A (p8A) | 462 (39%) |
| 936A (p28A) | 908 (76%) |

TABLE 2-continued

| Gene-introduced strain (Human animal cell expression vector) | Number of stained colonies (stained colonies/ total colonies) |
| --- | --- |
| PCDNA3 (pcDNA3) | 1196 (100%) |

As shown in Table 2, the cell growth of the gene-introduced strains 325S and 221S was inhibited to high degrees.

EXAMPLE 12

Evaluation of Activity (3)

1) Preparation of expression vectors

Human animal cell expression vector pΔNdeI was prepared in the same manner as in Example 10 1) except that a DNA fragment having the nucleotide sequence shown in SEQ ID NO:2 was cleaved with restriction enzyme NdeI and then ligated to give a DNA fragment deficient in nucleotides 319 to 426 (i.e. nucleotides coding for amino acids 64 to 99 in the amino acid sequence shown in SEQ ID NO: 2) in the nucleotide sequence shown in SEQ ID NO: 2.

Human animal cell expression vectors pE67A, pE70A, pE73A and pK78A were prepared respectively in the same manner as in Example 10 1) except that DNA fragments with those nucleotide sequences of SEQ ID NO: 2 where nucleotide A at the 330-position was replaced by C, nucleotide A at the 348-position by C, nucleotides AG at the 339- to 340-positions by CT, or nucleotides AAG at the 362- to 364-positions by GCT respectively were prepared by in vitro mutagenesis using PCR [Gene, 77, 51–59 (1989)]. Proteins obtained respectively by expressing pE67A, pE70A, pE73A and pK78A are proteins shown in SEQ ID NO: 1 in which amino acid residues at 67-, 70-, 73- and 78-positions, i.e. electrically charged Glu or Lys, have been replaced by charge-free Ala.

Human animal expression vectors p320a and p400a were prepared in the same manner as in Example 10 1) except that DNA fragments with those nucleotide sequence of SEQ ID NO: 2 where A was inserted next to nucleotide T at the 319-position or A was inserted next to nucleotide A at the 399-position were prepared by in vitro mutagenesis using PCR [Gene, 77, 51–59 (1989)]. The protein obtained by expressing p320a is a protein consisting of 66 residues which is the same as the amino acid sequence of SEQ ID NO: 1 in respect of the partial amino acid sequence at the 1- to 63-positions but is different by frame shifting in respect of the amino acid sequence at the 64- to 66-positions which are Asn, Asp and Cys respectively. The protein obtained by expressing p400a is a protein consisting of 92 residues which is the same as the amino acid sequence of SEQ ID NO: 1 in respect of the amino acid sequence at the 1- to 89-positions but is different by frame shifting in respect of the amino acid sequence at the 90- to 92-positions which are Lys, Phe and Trp respectively.

2) Transfection

Vero cells were transfected in the same manner as in Example 11 2) with human animal cell expression vectors p38 and p38A obtained in Example 10 1) and human animal cell expression vectors pΔNdeI, pE67A, pE70A, pE73A, pK78A, p320a and p400a obtained in 1) above as well as pcDNA3, whereby gene-introduced strains 325S, 325A, ΔNdeI, E67A, E70A, E73A, K78A, 320a, 400a and PCDNA3 were prepared respectively. 3) Measurement of growth inhibitory activity The cells were cultured in the same manner as in Examples 11 3). After culturing, the resulting colonies were fixed in PBS containing 10% formalin at room temperature for 30 minutes and stained with 0.1% aq. Crystal Violet at room temperature for 10 minutes, and then the number of stained colonies was counted. The results are shown in Table 3.

TABLE 3

| Gene-introduced strain (Human animal cell expression vector) | Number of stained colonies (stained colonies/ total colonies) |
| --- | --- |
| 325S (p38) | 15 (2%) |
| 325S (p38A) | 718 (102%) |
| ΔNdeI (p ΔNdeI) | 398 (57%) |
| E67A (pE67A) | 33 (5%) |
| E70A (pE70A) | 320 (45%) |
| E73A (pE73A) | 179 (25%) |
| K78A (pK78A) | 164 (23%) |
| 320a (p320a) | 548 (78%) |
| 400a (p400a) | 74 (11%) |
| PCDNA3 (pcDNA3) | 704 (100%) |

As shown in Table 3, the cell growth of gene-introduced strains 325S, E67A and 400a was inhibited to high degrees. Although the inhibitory effect on cell growth of E70A, E73A, and K78A was observed, this inhibitory effect was lower than that of E67A.

EXAMPLE 13

An Injection

One g of ETI-1 are dissolved in 100 g of refined soybean oil, and 12 g of refined egg yellow lecithin and 25 g of glycerin for injection are added to it. The mixture are adjusted to 1,000 ml with distilled water for injection, kneaded, and emulsified in a usual manner. The resulting suspension are sterilized by filtration through a 0.2 μm disposal type membrane filter and filled aseptically in a glass vial in an amount of 2 ml per vial to give an injection with the following formulation.

| | |
|---|---|
| ETI-1 | 2 mg |
| Refined soybean oil | 200 mg |
| Refined egg yellow lecithin | 24 mg |
| Glycerin for injection | 50 mg |
| Distilled water for injection | 1.72 ml |

EXAMPLE 14

Tablets

| | |
|---|---|
| ETI-1 | 100 g |
| Lactose | 40 g |
| Corn starch | 18 g |
| Carboxymethylcellulose calcium | 10 g |

Ten % hydroxypropylcellulose solution is added to and kneaded with the above mixture. This kneaded liquid is formed into granules through an extrusion granulator equipped with a 1.0 mm basket, and magnesium stearate is added thereto to form granules for compression which is then formed into tablets of 8 mm in diameter, each tablet (170 mg) containing 100 mg ETI-1.

EXAMPLE 15

Capsules

| | |
|---|---|
| ETI-1 | 50 g |
| Lactose | 80 g |
| Potato starch | 38 g |

Ten % hydroxypropylcellulose solution is added to and kneaded with the above mixture. It is formed into granules in the same manner as in Example 14, and magnesium stearate is added thereto to form capsules, each capsule (170 mg) containing 50 mg ETI-1 in a usual manner.

EXAMPLE 16

Soft Capsules

ETI-1 (10 g) is dissolved in soybean oil (100 g) and the resulting solution is introduced in a usual manner into capsules to give soft capsules, each containing 10 mg ETI-1.

INDUSTRIAL APPLICABILITY

According to the present invention, there can be provided a polypeptide useful as anti-tumor agent having the activity of inhibiting the growth of tumor cells and a gene coding for said polypeptide.

What is claimed is:

1. An isolated polypeptide consisting of the amino acid sequence of SEQ ID NO: 5 or 10.

2. An isolated polypeptide comprising an amino acid sequence of SEQ ID No. 5, said polypeptide having an activity of inhibiting growth of tumor cells.

3. An isolated DNA coding for a polypeptide as described in claim 1 or 2.

4. An isolated DNA which hybridizus at 42° C. with DNA consisting of the nucleotide sequence of SEQ ID NO: 1 or with an oligonucleotide probe prepared based on said nucleotide sequence in a solution containing 50% formamide, 5×SSPE, 5×Denhalt solution, 0.5% SDS and 100 µg/ml salmon sperm DNA, wherein said isolated DNA encodes a polypeptide having cell growth inhibitory activity.

5. An isolated DNA which hybridizes at 42° C. with DNA consisting of the nucleotide sequence of SEQ ID NO: 2 or with an oligonucleotide probe prepared based on said nucleotide sequence in a solution containing 50% formamide, 5×SSPE, 5×Denhalt solution, 0.5% SDS and 100 µg/ml salmon sperm DNA, wherein said isolated DNA encodes a polypeptide having cell growth inhibitory activity.

6. A recombinant vector comprising DNA as described in claim 4 or 5.

7. A transformant obtained by introducing a recombinant vector as described in claim 6 into host cells.

8. A process for producing a polypeptide comprising culturing a transformant as described in claim 7 in a medium, forming and accumulating said polypeptide in the culture, and recovering said polypeptide from the culture.

9. A pharrmaceutical composition comprising as an active ingredient a polypeptide as described in claim 1 or 2.

10. An anti-tumor agent comprising as an active ingredient a polypeptide as described in claim 1 or 2.

11. A method of inhibiting or treating tumors comprising administering an effective amount of a polypeptide as described in claim 1 or 2.

12. An isolated polypeptide comprising an amino acid sequence of SEQ ID NO. 5, wherein said polypeptide has any 85 to 309 consecutive amino acid sequence of SEQ ID NO. 10, said polypeptide having an activity of inhibiting growth of tumor cells.

* * * * *